US006310215B1

(12) United States Patent
Iwamoto (10) Patent No.: US 6,310,215 B1
(45) Date of Patent: Oct. 30, 2001

(54) PYRAZOLONE COMPOUNDS AND OPHTHALMIC PLASTIC LENS USING THE SAME

(75) Inventor: Hidetoshi Iwamoto, Tokyo (JP)

(73) Assignee: Hoya Healthcare Corporation, Tokyo (JP)

( * ) Notice: Subject to any disclaimer, the term of this patent is extended or adjusted under 35 U.S.C. 154(b) by 0 days.

(21) Appl. No.: 09/542,943

(22) Filed: Apr. 4, 2000

(30) Foreign Application Priority Data

Apr. 7, 1999 (JP) .................................................. 11-099685

(51) Int. Cl.7 .......................... G02C 7/04; C07D 403/06; A61K 31/4152; A61P 27/02
(52) U.S. Cl. ........................ 548/365.4; 351/160; 351/161; 351/162; 351/165; 548/365.4; 514/403
(58) Field of Search ........................ 548/365.4; 514/403; 351/160, 165, 162, 161, 159

(56) References Cited

U.S. PATENT DOCUMENTS

| 4,440,852 | * | 4/1984 | Onishi et al. ........................ 430/522 |
| 4,833,246 | * | 5/1989 | Adachi et al. ........................ 544/82 |
| 6,197,226 | * | 3/2001 | Amagni et al. ....................... 261/1.1 |
| 6,224,945 | * | 4/2001 | Calderara ............................ 427/353 |

FOREIGN PATENT DOCUMENTS

| 03208043 | * | 11/1991 | (JP) . |
| 7-24052 | | 1/1995 | (JP) . |
| 8-311045 | | 11/1996 | (JP) . |
| 10-195324 | | 7/1998 | (JP) . |

* cited by examiner

Primary Examiner—Floyd D. Higel
Assistant Examiner—Andrea M. D'Souza
(74) Attorney, Agent, or Firm—Nixon & Vanderhye (57) ABSTRACT

Provided are novel pyrazolone compounds which have excellent copolymerizability and undergo no elution in an organic solvent when used for an ophthalmic plastic lens and which have an excellent absorption peak in visible light region and function as a reactive yellow dye.

40 Claims, 5 Drawing Sheets

PYRAZOLONE COMPOUNDS AND OPHTHALMIC PLASTIC LENS USING THE SAME

TECHNICAL FIELD

The present invention relates to a novel pyrazolone compound, an ophthalmic plastic lens using it and a process for producing an ophthalmic plastic lens. More specifically, the present invention relates to a novel pyrazolone compound which has two functions, capability of reacting with a polymerizable monomer and capability of coloring an obtained polymer in yellow, and which is useful for coloring an ophthalmic plastic lens, an ophthalmic plastic lens using the above pyrazolone compound, particularly, an intraocular lens such as a soft intraocular lens which can be easily inserted through a small incision, and a process for efficiently producing the above ophthalmic plastic lens.

BACKGROUND ART

A crystalline lens gets colored in yellow as people get old, and the color becomes denser. When the crystalline lens so-colored in yellow is removed, no filter effect works, and there appears a phenomenon that objects look bluish. This phenomenon is called Ocyanopsian, and it is a cyanopsia-correcting intraocular lens colored in yellow that corrects the above phenomenon to bring the vision close to the normal vision. As the above cyanopsia-correcting intraocular lens, there has been used a hard lens made of polymethyl methacrylate (PMMA).

In recent years, there has been developed a small incision operating method which aims at a simple operation, a decrease in the occurrence of astigmatism after the operation and sooner recovery therefrom. A soft intraocular lens attracts attention as a lens for the above small incision operation, which soft intraocular lens is made of a silicone or acrylic material and can be inserted through a small incision in a folded state. However, no soft intraocular lens which works to correct cyanopsia has been commercially available. The reason therefor is that when a soluble or dispersible colorant for the above hard lens made of PMMA is used in a soft material, there is caused a big problem that the colorant bleeds out. The bleeding-out is a phenomenon that the internal molecular chain of a soft material undergoes intense motion due to a low glass transition temperature of the soft material so that a dissolved or dispersed colorant migrates onto a lens surface.

For overcoming the above problem, for example, there has been proposed a soft intraocular lens, in which an ultraviolet absorbent and a yellow dye are decreased in amount for controlling the elution of these (JP-A-7-24052). However, the above soft intraocular lens is not yet satisfactory.

As an ultraviolet absorbent, there is known a compound having a monomer structure which permits copolymerization with a monomer for a lens. For example, there is disclosed a reactive ultraviolet absorbent having a benzotriazole structure and having excellent copolymerizability and hydrolysis resistance (JP-A-8-311045). Further, as a reactive yellow dye, there has been disclosed an azobenzene-based yellow dye (Japanese PCT Publication No. 8-503997). The use of the above ultraviolet absorbent or yellow dye having a monomer structure is indispensable to ophthalmic lenses such as a hydrous contact lens and an oxygen-permeable hard contact lens, particularly to a soft intraocular lens.

As a reactive ultraviolet absorbent, a variety of compounds have been developed from the viewpoint of absorption spectrum, solubility, reactivity and durability. However, as a reactive yellow dye, few compounds have been developed, or no satisfactory compound is available.

For example, a compound of the formula (II) is known as a reactive yellow dye (JP-A-10-195324).

(II)

The above compound is satisfactory in view of solubility in various monomers for lenses and copolymerizability therewith. However, the above compound has problems that it has a maximum absorption of spectrum in approximately 350 to 360 nm and that its molecular extinction coefficient is relatively small. That is, the above compound is insufficient in absorption of light in a region of from 400 nm to 500 nm, which absorption is considered effective for correcting cyanopsia. Another problem is that the amount of the above compound to be used is relatively large when it is used.

In view of safety and the filter effect, there has been desired a reactive dye which exhibits a sufficient filter effect when a low concentration of it is added. This point is very important for a contact lens which is to come in contact with corneal mucosa and an intraocular lens which is to be implanted in an eye.

Under the circumstances, it is an object of the present invention to provide a novel compound which is excellent in solubility in a monomer for a lens and copolymerizability with the monomer, which undergoes no elution during extraction with various solvents, which has an excellent absorption peak in a visible light region when used in an ophthalmic plastic lens and which works sufficiently in a small amount.

It is another object of the present invention to provide an ophthalmic plastic lens, particularly an intraocular lens such as a soft intraocular lens, to which the above novel compound is applied.

Further, it is another object of the present invention to provide a process for efficiently producing the above ophthalmic plastic lens.

DISCLOSURE OF THE INVENTION

The present inventor has made diligent studies to achieve the above objects and as a result has found that a compound having a specific structure can fulfill the above objects as a reactive yellow dye. It has been also found that an ophthalmic plastic lens, particularly, an intraocular lens such as a soft intraocular lens, can be efficiently produced by providing a polymerizable material containing the above compound and a monomer for a lens, polymerizing the polymerizable material by a specific method and optionally, cutting and polishing an obtained polymerizate. On the basis of the above findings, the present invention has been completed.

That is, according to the present invention, there are provided;

(1) A pyrazolone compound having the formula (I), (I)

wherein X is phenyl or 4-alkylphenyl, (2) an ophthalmic plastic lens formed by polymerizing a polymerizable material containing the pyrazolone compound of the above formula (I) and a monomer for lens, preferably, an intraocular lens comprising an optic portion including an essential portion formed of the pyrazolone compound of the above formula (I), particularly preferably a soft intraocular lens, (3) a process for the production of an ophthalmic plastic lens, which comprises casting a polymerizable material containing the pyrazolone compound of the above formula (I) and a monomer for a lens into a predetermined mold and polymerizing the polymerizable material, and (4) a process for the production of an ophthalmic plastic lens, which comprises casting a polymerizable material containing the pyrazolone compound of the formula (I) and a monomer for a lens into a central hollow portion of a hard polymer material shaped in the form of a doughnut, polymerizing the polymerizable material and then cutting and polishing a polymerizate integrated with said hard polymer material, to form a hard haptic portion and a soft optic portion.

BEST MODE FOR CARRYING OUT THE INVENTION

The pyrazolone compound of the present invention is a novel compound having the following formula (I).

(I)

In the formula (I), X is phenyl or 4-alkylphenyl, and specific examples thereof include p-tolyl, 4-ethylphenyl, 4-n-propylphenyl, 4-isopropylphenyl, 4-n-butylphenyl, 4-isobutylphenyl, 4-sec-butylphenyl and 4-tert-butylphenyl.

The compound of the above formula (I) has ketoenol tautomerism. The compound of the formula (I) provided by the present invention therefore includes these tautomers.

wherein X is as defined above.

The above pyrazolone compound of the formula (I) is a reactive yellow dye having excellent solubility in, and copolymerizability with, a monomer for a lens and having excellent light absorption spectrum in the region of 400 to 500 nm. When incorporated into an ophthalmic plastic lens by copolymerization, the above pyrazolone compound not only can color the lens in yellow but also is free from bleeding out from the lens, and further, it undergoes no elution during procedures of extraction with various solvents.

The method of producing the above pyrazolone compound of the formula (I) is not specially limited. For example, it can be produced according to the following reaction scheme.

wherein X is as defined above.

First, methacryloyl chloride (III) and 3-amino-1-phenyl-2-pyrazoline-5-one (IV) are reacted in a solvent containing a hydrogen chloride scavenger or in a hydrogen chloride scavenging solvent such as anhydrous pyridine, to form 1-phenyl-3-methacrylamide-5-pyrazolone (V). Then, the 1-phenyl-3-methacrylamide-5-pyrazolone (V) is reacted with 1-aryl-3-methyl-5-oxo-2-pyrazoline-4-carboaldehyde (VI) in the presence of an acid catalyst, whereby the compound of the formula (I) as an end product can be obtained.

In the above reactions, a commercially available methacryloyl chloride is used as a raw material, and desirably, it is used upon distillation. The 1-aryl-3-methyl-5-oxo-2-pyrazoline-4-carboaldehyde (VI) can be obtained by reacting 1-aryl-3-methyl-2-pyrazoline-5-one with phosphorus oxychloride in dimethylformamide.

The acid catalyst can be selected from organic acids such as alkyl-substituted benzenesulfonic acids typified by p-toluenesulfonic acid, etc., and inorganic acids such as sulfuric acid, hydrochloric acid and phosphoric acid. A solvent used for the reaction between the compounds (VI) and (V) includes alcohols typified by methanol, ethanol, propanol, etc., diethyl ether, methylene chloride and 1,2-dichloromethane. These solvents may be used alone or in combination.

The ophthalmic plastic lens of the present invention is a product produced by polymerizing a polymerizable material containing the pyrazolone compound of the formula (I) and a monomer for a lens. The product is preferably an intraocular lens, and it is particularly preferably a soft intraocular lens.

Examples of the above monomer for a lens include linear or branched alkyl (meth)acrylates (the term "(meth)acrylaten" refers to both of acrylate and methacrylate, and used in this sense hereinafter) such as methyl methacrylate, ethyl methacrylate, butyl (meth)acrylate, cyclohexyl methacrylate, lauryl (meth)acrylate, ethylhexyl (meth)acrylate and phenylethyl (meth)acrylate; hydrophilic monomers typified by 2-hydroxyethyl methacrylate, N-vinylpyrrolidone, dimethylacrylamide and methacrylic acid; silicon-containing monomers typified by tris(trimethylsiloxy)silylpropyl (meth)acrylate, trimethylsiloxydimethylsilylpropyl (meth)acrylate and bis(trimethylsiloxy)methylsilylpropyl (meth)acrylate; and fluorine-containing monomers typified by trifluoroethyl (meth)acrylate, hexafluoroisopropyl (meth)acrylate, perfluorooctylethyloxypropylene (meth)acrylate. These monomers may be used alone or in combination. Further, there may be added (meth)acrylate of a dihydric or higher polyhydric alcohol as a crosslinking agent. The (meth)acrylate of a dihydric or higher polyhydric alcohol includes monomers typified by ethylene glycol di(meth)acrylate, diethylene glycol di(meth)acrylate, triethylene glycol di(meth)acrylate and trimethylolpropane tri(meth)acrylate.

In the polymerizable material, the amount ratio of the pyrazolone compound of the formula (I)/the monomer for a lens is preferably 0.005/100 to 0.10/100 (w/w), particularly preferably 0.01/100 to 0.05/100 (w/w).

The above polymerizable material may contain an ultraviolet absorbent and a polymerization initiator. As an ultraviolet absorbent, although not to be specially limited, any ultraviolet absorbent may be used so long as it does not undergo elution and bleeding-out. However, it is preferred to use an ultraviolet absorbent having a monomer structure. The ultraviolet absorbent having a monomer structure is preferably selected from benzotriazole ultraviolet absorbents such as compounds having the following formulae, and benzophenone ultraviolet absorbents such as 2-hydroxy-4-acryloyloxyethoxybenzophenone. These ultraviolet absorbents may be used alone or in combination. The amount of the ultraviolet absorbent based on the monomer for a lens is preferably 0.05 to 5.0% by weight, particularly preferably 0.5 to 3.0% by weight.

The polymerization initiator is not critical, and it can be selected from generally known radical initiators, including peroxides such as lauroyl peroxide, bis(4-tert-butylcyclohexyl)peroxydicarbonate and 1,1-bis(tert-butylperoxy)-3,3,5-trimethylcyclohexane, and azo compounds such as 2,2'-azobisisobutyronitrile, 2,2'-azobis(2,4-dimethylvaleronitrile), 2,2'-azobis(4-methoxy-2,4-dimethylvaleronitrile) and 2,2'-azobis[2-(2-imidazoline-2-yl)propane. Further, a photopolymerization initiator may be used. The amount of the polymerization initiator based on the monomer for a lens is preferably 0.05 to 2.0% by weight, particularly preferably 0.1 to 0.8% by weight.

The method for producing the ophthalmic plastic lens of the present invention is not specially limited. However, the ophthalmic plastic lens of the present invention can be efficiently produced according to the following process.

The process of the present invention includes two embodiments. In a first method, the polymerizable material containing the pyrazolone compound of the formula (I) and the monomer for a lens and containing am ultraviolet absorbent and a polymerization initiator as required is cast into a shaping mold made, for example, of a metal, plastic or glass in the form of a rod, a plate, a lens, or the like, and the polymerizable material is polymerized by increasing the temperature thereof, preferably, stepwise continuously. In this case, oxygen, etc., in the polymerizable material is replaced with an inert gas such as nitrogen, argon or helium as required, and the mold is closed before the polymerization. An obtained polymerizate is cut and polished as required, to finish it in a lens form. In the above polymerization, the polymerization may be carried out with light such as ultraviolet light or visible light as required.

In a second method, a hard polymer material is shaped in the form of a doughnut in advance, and the above polymerizable material is cast into a central hollow portion and polymerized in the same manner as in the above first method. Then, a polymerizate integrated with the above hard polymer material is cut and polished to form a hard haptic portion and a soft optic portion, whereby an ophthalmic plastic lens is produced. The above hard polymer material may be a colored product.

In the ophthalmic plastic lens of the present invention, the lens or the optic portion may be modified to have a hydrophilic surface by plasma-treating it with oxygen or air and immersing it in a reducing bath such as an aqueous solution containing sodium thiosulfate.

The thus-produced ophthalmic plastic lens of the present invention is not only colored in yellow but also free of bleeding-out a dye (compound of the formula (I)) and elution caused by a solvent. Further, it has a sufficient light absorption in a wavelength region of 400 to 500 nm and is remarkably useful as a cyanopsia-correcting lens.

EXAMPLES

The present invention will be explained more in detail with reference to Examples hereinafter, while the present invention shall not be limited by these Examples.

Measuring machines, and the like used in Examples are as follows.

Elemental analysis: CHN recorder MT-3 (Yanagimoto Seisakusho).

HPLC analysis: HPLC D-6100 system, supplied by Hitachi Ltd.

Column: ODS-2 (5 microns)

Infrared absorption spectrum: Fourier transform infrared spectrophotometer FT-700 (K.K. Horiba Seisakusho) Light transmittance factor and ultraviolet-visible light spectrum: Automatic spectrophotometer U-3210 (Hitachi Ltd.)

Example 1

(Preparation of pyrazolone compound of the formula (I), reactive yellow dye)

(1) Preparation of 3-methyl-5-oxo-1-phenyl-2-pyrazoline-4-carboaldehyde (MPCA)

29 Grams of 3-methyl-1-phenyl-2-pyrazoline-5-one and 40 ml of dimethylformamide were charged into a 200-ml three-necked flask, stirred and cooled to 0° C. in an ice-acetone bath. Then, 18.5 g of phosphorus oxychloride (POCl$_3$) was placed in a dropping funnel, and while it was maintained at 10 to 20° C., it was dropwise added. After the addition, the mixture was heated for 1 hour, then, a reaction mixture was poured into 600 ml of ice water, and the mixture was allowed to stand for one day and night. A crystal was recovered by suction filtration, fully washed with water and dried to give the captioned compound. Yield: 65%, Melting point: 178–180° C. (documented value: 174–175° C.).

Corresponding other aldehyde derivatives were also prepared in the same manner as above.

(2) Preparation of 1-phenyl-3-methacrylamide-5-pyrazolone (PMAP)

17 Grams of 1-phenyl-3-amino-5-pyrazolone and 100 ml of pyridine (anhydrous) were charged into a 300-ml three-necked flask, and the stirring of the mixture was initiated at room temperature. 21 Grams of methacryloyl chloride was placed in a dropping funnel and dropwise added to the above reaction mixture slowly. After the addition, the mixture was stirred for one day and night. The reaction mixture was poured into 500 ml of ice water, the resultant mixture was allowed to stand for one day and night, and a crystal was recovered by suction filtration, fully washed with water and recrystallized from ethanol, to give a captioned compound. Yield: 60%, Melting point: 170° C. (Reference document: UK Patent 875248).

(3) Preparation of 4-(5-hydroxy-3-methyl-1-phenyl-4-pyrazolylmethylene)-3-methacrylamino-1-phenyl-2-pyrazoline-5-one (HMPO-H, compound of the formula (I) in which X is phenyl).

0.95 Gram of MPCA obtained in the above (1), 1.2 g of PMAP obtained in the above (2), 100 mg of p-toluenesulfonic acid monohydrate and 30 ml of an ethanol/methylene chloride mixture (weight ratio 4/6) were charged into a 50-ml egg plant type flask and stirred at room temperature for 24 hours. As the reaction proceeded, the reaction mixture became colored in yellow. An acid was neutralized with a sodium hydrogencarbonate aqueous solution, then, the solvent was removed with an evaporator, and a precipitated yellow solid was recovered by suction filtration, fully washed with water and then washed with methanol and hexane. The thus-obtained crystal was dissolved in dimethyl sulfoxide (DMSO), a small amount of water was added to re-precipitate the crystal, and the crystal was fully washed with water and hexane and then dried under reduced pressure to give a captioned compound. Yield: 90%, Melting point: 243–246° C.

IR (KBr): 3255 cm$^{-1}$, 1666 cm$^{-1}$, 1614 cm$^{-1}$, 1587 cm$^{-1}$.

Elemental Analysis:
Calculated (as $C_{24}H_{21}N_5O_3$); C 67.44, H 4.95, N 16.38%
Found; C 67.54, H 5.05, N 16.46%
HPLC analysis (methanol/water=9/1): RT 2.80 min. purity 99.5%

Figure 1:
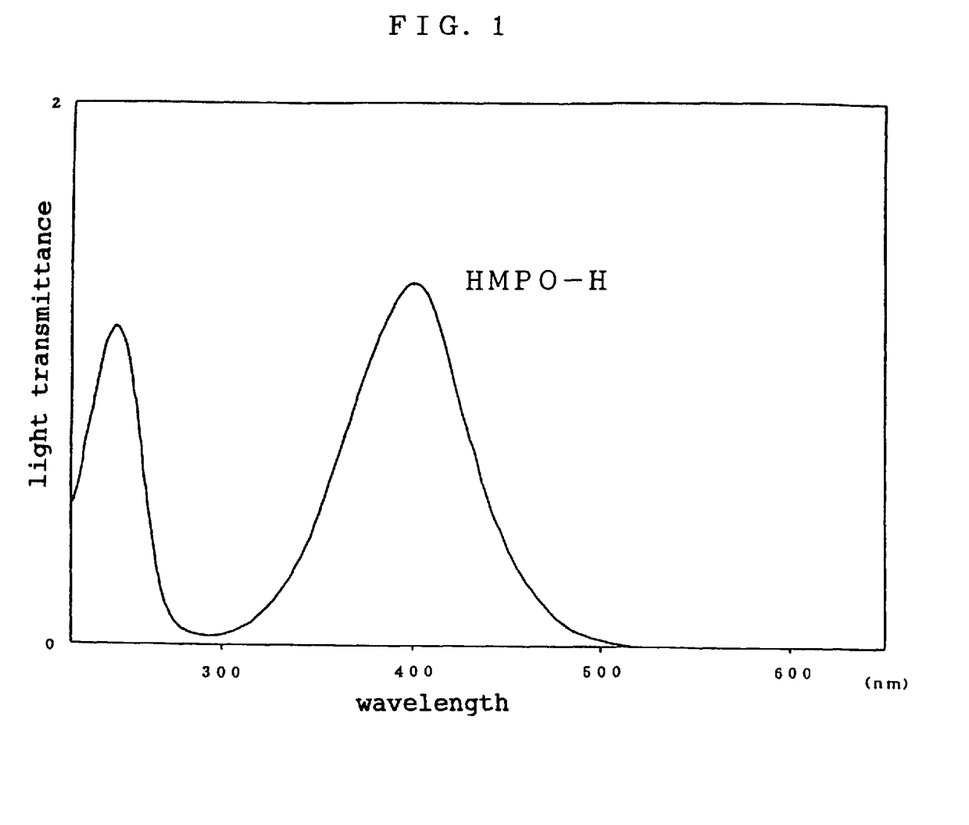
FIG. 1 shows an ultraviolet-visible light absorption spectrum of one example of the compound of the formula (I) provided by the present invention.

FIG. 1 shows ultraviolet-visible light absorption spectrum (dichloroethane).

Other compounds of the formula (I) were also prepared in the same manner. The structures of these compounds are shown below.

Example 2

(Production of ophthalmic plastic lens)

Figure 2:
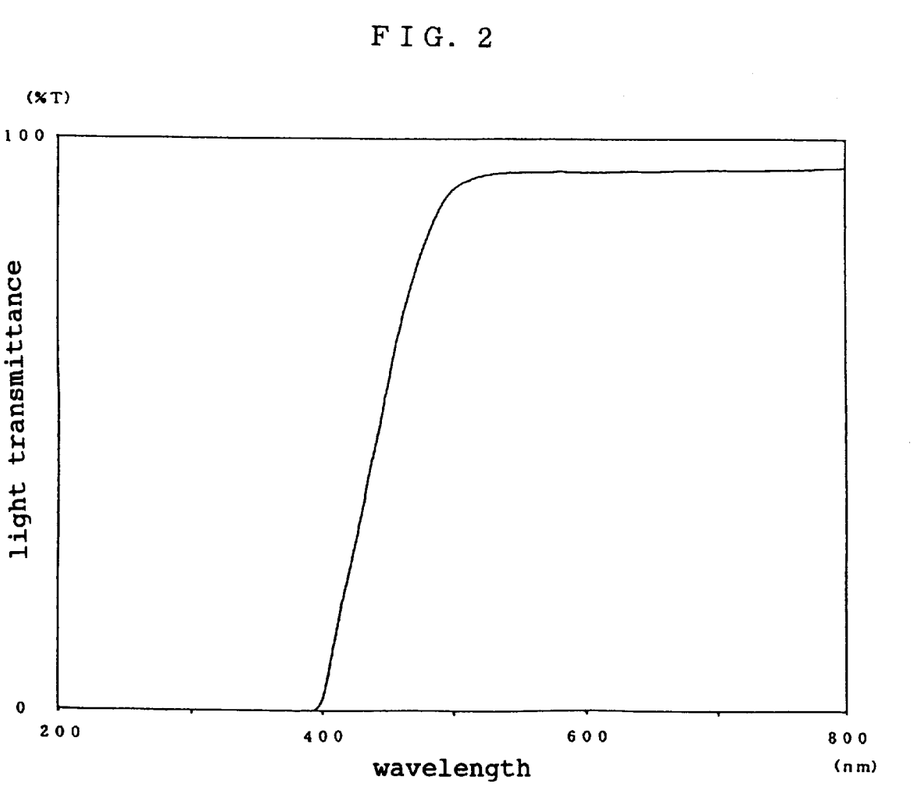
FIG. 2 shows a light transmittance curve of an ophthalmic plastic lens obtained in Example 2.

A mixture containing 42 g of n-butyl acrylate (n-BA), 52 g of phenylethyl methacrylate (PEMA), 8 g of perfluorooctylethyloxypropylene methacrylate (HRM-5131HP), 5 g of ethylene glycol dimethacrylate (EDMA) and 0.33 g of 2,2'-azobisisobutyronitrile (AIBN) was provided. To the mixture were added 1.50% by weight, based on the total amount of monomers for a lens, of an ultraviolet absorbent T-150 and 0.02% by weight, based on the total amount of the monomers, of the reactive yellow dye HMPO-H included in the compound of the formula (I). The resultant mixture was fully stirred with passing nitrogen gas, to obtain a polymerizable material. The polymerizable material was placed in a PP resin mold designed for producing an intraocular lens optic portion, and thermally polymerized according to a predetermined polymerization program. The so-obtained lenses were immersed in each of 10 ml of methanol, 10 ml of acetone and 10 ml of hexane at room temperature for 72 hours (10 lenses were immersed in methanol, 10 lenses were immersed in acetone and 10 lenses were immersed in hexane). Then, the solvents were measured for ultraviolet-visible light absorption spectrum. As a result, the elusion of the HMPO-H which was a yellow dye was not found in any solvent. Further, the obtained lenses were measured for a light transmittance to show a remarkably excellent light transmittance curve. FIG. 2 shows the light transmittance curve.

Example 3

(Production of ophthalmic plastic lens)

To a mixture of 70 g of 2-hydroxyethyl methacrylate (HEMA) with 0.25 g of AIBN was added 0.015% by weight, based on the monomer for a lens, of the reactive yellow dye HMPO-H included in the compound of the formula (I), and the resultant mixture was fully stirred to obtain a polymerizable material. The polymerizable material was cast into a gasket made of polyethylene having a diameter of 15 mm and a height of 15 mm, then, heat-sealed and thermally polymerized at 60° C. for 12 hours, at 90° C. for 3 hours and at 100° C. for 12 hours, to give a polymerizate having the form of a button. The polymerizate was cut to a thickness of 1 mm, and the thus-prepared pieces were immersed in each of 10 ml of methanol, 10 ml of acetone and 10 ml of hexane at room temperature for 72 hours (10 pieces were immersed in methanol, 10 pieces were immersed in acetone and 10 pieces were immersed in hexane). Then, the solvents were measured for ultraviolet-visible light absorption spectrum. As a result, the elution of the HMPO-H which was a yellow dye was not found in any solvent. Further, the obtained lenses were measured for a light transmittance to show a remarkably excellent light transmittance curve.

Example 4
(Production of ophthalmic plastic lens)

A mixture containing 42 g of n-butyl acrylate (n-BA), 52 g of phenylethyl methacrylate (PEMA), 8 g of perfluorooctylethyloxypropylene methacrylate (HRM-5131HP), 5 g of ethylene glycol dimethacrylate (EDMA) and 0.33 g of AIBN was provided. To the mixture were added 1.5% by weight, based on the total amount of the monomers for a lens, of an ultraviolet absorbent T-150 and 0.02% by weight, based on the total amount of the monomers, of the reactive yellow dye HMPO-B included in the compound of the formula (I). The resultant mixture was fully stirred with passing nitrogen gas, to obtain a polymerizable material. The polymerizable material was placed in a PP resin mold designed for producing an intraocular lens optic portion, and thermally polymerized according to a predetermined, polymerization program. The so-obtained lenses were immersed in each of 10 ml of methanol, 10 ml of acetone and 10 ml of hexane at room temperature for 72 hours (10 lenses were immersed in methanol, 10 lenses were immersed in acetone and 10 lenses were immersed in hexane). Then, the solvents were measured for ultraviolet-visible light absorption spectrum. As a result, the elusion of the HMPO-B which was a yellow dye was not found in any solvent. Further, the obtained lenses were measured for a light transmittance to show a remarkably excellent light transmittance curve.

Example 5
(Production of ophthalmic plastic lens)

To a mixture of 70 g of 2-hydroxyethyl methacrylate (HEMA) with 0.25 g of a polymerization initiator [2,2'-azobis(2,4-dimethylvaleronitrile), trade name: V-65, supplied by Wako Purechemicals K.K.] were added 1.0% by weight, based on the monomer for a lens, of an ultraviolet absorbent CVPT and 0.015% by weight, based on the monomer for a lens, of the reactive yellow dye HMPO-M included in the compound of the formula (I), and the resultant mixture was fully stirred to obtain a polymerizable material. The polymerizable material was cast into a gasket made of polyethylene having a diameter of 15 mm and a height of 15 mm, then, heat-sealed and thermally polymerized at 60° C. for 12 hours, at 90° C. for 3 hours and at 100° C. for 12 hours, to give a polymerizate having the form of a button. The polymerizate was cut to a thickness of 1 mm, and the thus-prepared pieces were immersed in each of 10 ml of methanol, 10 ml of acetone and 10 ml of hexane at room temperature for 72 hours (10 pieces were immersed in methanol, 10 pieces were immersed in acetone and 10 pieces were immersed in hexane). Then, the solvents were measured for ultraviolet-visible light absorption spectrum. As a result, the elution of the HMPO-M which was a yellow dye was not found in any solvent. Further, the obtained lenses were measured for a light transmittance to show a remarkably excellent light transmittance curve.

Example 6

A mixture containing 42 g of n-butyl acrylate (n-BA), 52 g of phenylethyl methacrylate (PEMA), 8 g of perfluorooctylethyloxypropylene methacrylate (HRM-5131HP), 5 g of ethylene glycol dimethacrylate (EDMA) and 0.33 g of AIBN was provided. To the mixture were added 1.5% by weight, based on the total amount of the monomers for a lens, of an ultraviolet absorbent CVPT and 0.02% by weight, based on the total amount of the monomers for a lens, of the reactive yellow dye HMPO-H included in the compound of the formula (I). The resultant mixture was fully stirred with passing nitrogen gas, to obtain a polymerizable material. The polymerizable material was placed in a PP resin mold designed for producing an intraocular lens optic portion, and thermally polymerized according to a predetermined polymerization program. The so-obtained lenses were plasma-treated with a plasma-treating machine (PA-100AT, supplied by Kyoto Denshi Keisoku K.K.) using oxygen as a reaction gas. Then, the lenses were immersed in a 0.5% by weight of sodium thiosulfate aqueous solution for 1.5 hours at 50° C. The lenses had surfaces remarkably excellent in wettability with water. Further, like the lenses obtained in Example 2, the lenses were free from the elution with any of the solvents used in Example 2, and the solvents were measured for ultraviolet-visible light absorption spectrum, to show no change.

Example 7

To a mixture of 98 g of methyl methacrylate (MMA) with 2 g of ethylene glycol dimethacrylate (EDMA) were added 0.03% by weight, based on the total amount of the monomers, of a reactive blue dye AQ-1 of the formula to be described later and 0.2% by weight, based on the total amount of the monomer, of AIBN, and the resultant mixture was fully stirred to obtain a polymerizable material. The polymerizable material was charged into a tube made of polyethylene having a size of 20 mm×20 cm, and the tube was closed. Then, the polymerizable material was polymerized according to a predetermined temperature program. The resultant polymerizate was cut in the form of a 7 mm-thick button, a portion located within 3 mm from the center of the button-shaped product was removed, to give a doughnut-shaped button made of polymethyl methacrylate (PMMA).

Then, a mixture containing 42 g of n-butyl acrylate (n-BA), 52 g of phenylethyl methacrylate (PEMA), 8 g of perfluorooctylethyloxypropylene methacrylate (HRM-5131HP), 5 g of ethylene glycol dimethacrylate (EDMA) and 0.33 g of AIBN was provided. To the mixture were added 1.5% by weight, based on the total amount of the monomers for a lens, of an ultraviolet absorbent CVPT and 0.02% by weight, based on the total amount of the monomers for a lens, of the reactive yellow dye HMPO-H, and the resultant mixture was fully stirred, to obtain a polymerizable material. The polymerizable material was added to the central portion of the above-prepared doughnut-shaped button made of PMMA, and thermally polymerized according to a predetermined polymerization program. The resultant polymerizate had a central portion (diameter 3 mm) formed of a soft material colored in yellow and a circumferential portion formed of a hard material colored in blue. Then, the polymerizate was cut and polished in the form of an intraocular lens, to give a one-piece soft intraocular lens having an optic portion formed of a soft yellow material and a haptic portion formed of PMMA. The obtained lens was measured for a light transmittance to show a remarkably excellent light transmittance curve.

AQ-1:

Comparative Example 1
(Production of comparative ophthalmic lens)

Figure 3:
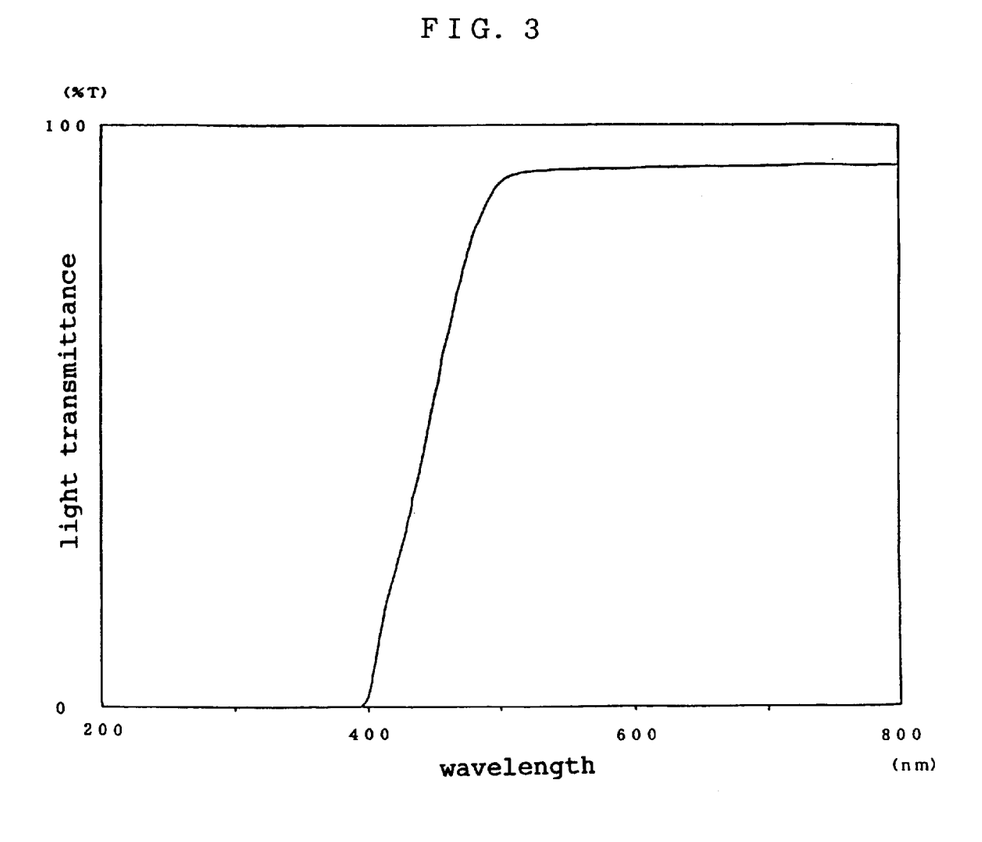
FIG. 3 shows a light transmittance curve of an ophthalmic plastic lens obtained in Comparative Example 1.

A mixture containing 42 g of n-butyl acrylate (n-BA), 52 g of phenylethyl methacrylate (PEMA), 8 g of perfluorooctylethyloxypropylene methacrylate (HRM-5131HP), 5 g of ethylene glycol dimethacrylate (EDMA) and 0.33 g of AIBN was provided. To the mixture were added 1.7% by weight, based on the total amount of the monomers for a lens, of an ultraviolet absorbent T-150 and 0.02% by weight, based on the total amount of the monomers for a lens, of a non-reactive yellow dye MY3G (C.I. Solvent Yellow 93). The resultant mixture was fully stirred with passing nitrogen gas, to obtain a polymerizable material. The polymerizable material was charged into a PP resin mold designed for producing an intraocular lens optical portion and polymerized according to a predetermined polymerization program. Obtained lenses were immersed in each of 10 ml of methanol, 10 ml of acetone and 10 ml of hexane at room temperature for 72 hours (10 lenses were immersed in methanol, 10 lenses were immersed in acetone and 10 lenses were immersed in hexane). As a result, the elution of the yellow dye was intense, or the elution rate thereof was 100% in hexane, 60% in methanol and 30% in acetone. FIG. 3 shows a light transmittance curve of the obtained lens.

Comparative Example 2
(Production of comparative ophthalmic lens)

Figure 4:
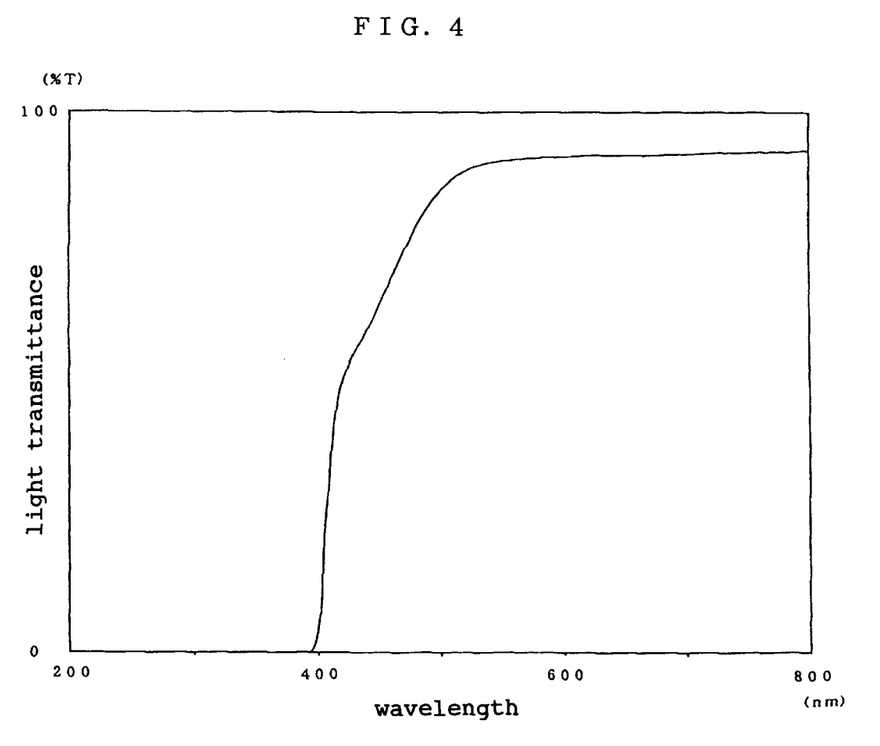
FIG. 4 shows a light transmittance curve of an ophthalmic plastic lens obtained in Comparative Example 2.

A mixture containing 42 g of n-butyl acrylate (n-BA), 52 g of phenylethyl methacrylate (PEMA), 8 g of perfluorooctylethyloxypropylene methacrylate (HRM-5131HP), 5 g of ethylene glycol dimethacrylate (EDMA) and 0.33 g of AIBN was provided. To the mixture were added 1.5% by weight, based on the total amount of the monomers for a lens, of an ultraviolet absorbent T-150 and 0.2% by weight, based on the total amount of the monomers for a lens, of a reactive yellow dye VBCP-o having a formula to be described later. The resultant mixture was fully stirred with passing nitrogen gas, to obtain a polymerizable material. The polymerizable material was charged into a PP resin mold designed for producing an intraocular lens optical portion, and polymerized according to a predetermined polymerization program. Obtained lenses were immersed in each of 10 ml of methanol, 10 ml of acetone and 10 ml of hexane at room temperature for 72 hours (10 lenses were immersed in methanol, 10 lenses were immersed in acetone and 10 lenses were immersed in hexane). Then, each solvent was measured for ultraviolet-visible light absorption spectrum. As a result, the elution of the yellow dye was not found in any solvent. However, it was required to add the yellow dye in an amount 10 times as large as the amount of the reactive dye of the present invention for imparting the lens with a yellow color effective for correcting cyanopsia. FIG. 4 shows a light transmittance curve of the obtained lens.

VBCP-o

Comparative Example 3
(Production of comparative ophthalmic lens)

To a mixture of 70 g of 2-hydroxyethyl methacrylate (HEMA) with 0.21 g of a polymerization initiator V-65 were added 1.0% by weight, based on the monomer, of an ultraviolet absorbent CVPT and 0.02% by weight, based on the monomer, of a non-reactive yellow dye MY3G, and the resultant mixture was fully stirred to obtain a polymerizable material. The polymerizable material was cast into a gasket made of polyethylene having a diameter of 15 mm and a height of 15 mm, then, heat-sealed and thermally polymerized at 60° C. for 12 hours, at 90° C. for 3 hours and at 100° C. for 12 hours, to give a polymerizate having the form of a button. The polymerizate was cut to a thickness of 1 mm, and the thus-prepared pieces were immersed in each of 10 ml of methanol, 10 ml of acetone and 10 ml of hexane at room temperature for 72 hours (10 pieces were immersed in methanol, 10 pieces were immersed in acetone and 10 pieces were immersed in hexane). Each solvent was measured for ultraviolet-visible light absorption spectrum. As a result, the elution of the yellow dye was intense, or the elution rate thereof was 90% in acetone, 70% in methanol and 20% in hexane.

Example 8
(Production of ophthalmic plastic lens)

To a mixture of 32 g of n-butyl acrylate (n-BA), 60 g of phenylethyl methacrylate (PEMA), 8 g of perfluorooctylethyloxypropylene methacrylate (HRM-5131HP), 3 g of ethylene glycol dimethacrylate (EDMA) and 0.3 g of AIBN was added 0.150% by weight, based on the total amount of monomers for a lens, of an ultraviolet absorbent T-150 and 0.02% by weight, based on the monomer for a lens, of the reactive yellow dye HMPO-H included in the compound of the formula (I), and the resultant mixture was fully stirred to obtain a polymerizable material. The polymerizable material was cast into gasket made of polypropylene having a diameter of 15 mm and height of 15 mm, then, heat-sealed and thermally polymerized. The polymerization program was as follows. First the mixture was maintained at 40° C. for 10 minutes and then temperature-elevated to 60° C. in 40 minutes. Thereafter it was maintained at 60° C. for 4 hours and temperature-elevated to 80° C. in one hour, and it was maintained at the same temperature for 2 hours. After that, it was temperature-elevated to 100° C. in one hour and maintained at the same temperature for 2 hours. Finally it was temperature-elevated to 120° C. in one hour and maintained at the same temperature for 2 hours. After that, it was cooled slowly to 30° C. in six hours to give a polymerizate having the form of button. The polymerizate was cut to a thickness of 1 mm, and the thus-prepared pieces were immersed in each of 10 ml of methanol, 10 ml of acetone and 10 ml of hexane at room temperature for 72 hours (10 pieces were immersed in methanol, 10 pieces were immersed in acetone and 10 pieces were immersed in hexane). Then, the solvents were measured for ultraviolet-visible light absorption spectrum. As a result, the elusion of the HMPO-H which was a yellow dye was not found in any solvent. Further, the obtained lenses were measured for a light transmittance to show a remarkably excellent light transmittance curve.

Example 9

To a mixture of 90 g of methyl methacrylate (MMA), 10 g of n-butyl anylate (n-BA) and 2 g of ethylene glycol dimethacrylate (EDMA) were added 0.06% by weight, based on the total amount of the monomers, of a reactive blue dye AQ-1 of the formula to be described above and 0.3% by weight, based on the total amount of the monomer, of AIBN, and the resultant mixture was fully stirred to obtain a polymerizable material. The polymerizable material was charged into a tube made of polyethylene having a size of 20 mm×20 cm, and the tube was closed. Then, the polymerizable material was polymerized according to a predetermined temperature program.

That is, the tube in which the polymerizable material was contained was maintained at 40° C. for 4 hours and then temperature-elevated to 60° C. in 4 hours and maintained at the same temperature for 8 hours. After that, it was temperature-elevated to 110° C. in 10 hours and maintained at the same temperature for 8 hours. Finally it was slowly cooled to 40° C. in 20 hours to obtain a polymerizate for haptic portion. The resultant polymerizate was cut in the form of a 7 mm-thick button, a portion located-within 3 mm from the center of the button-shaped product was removed, to give a doughnut-shaped button.

Figure 5:
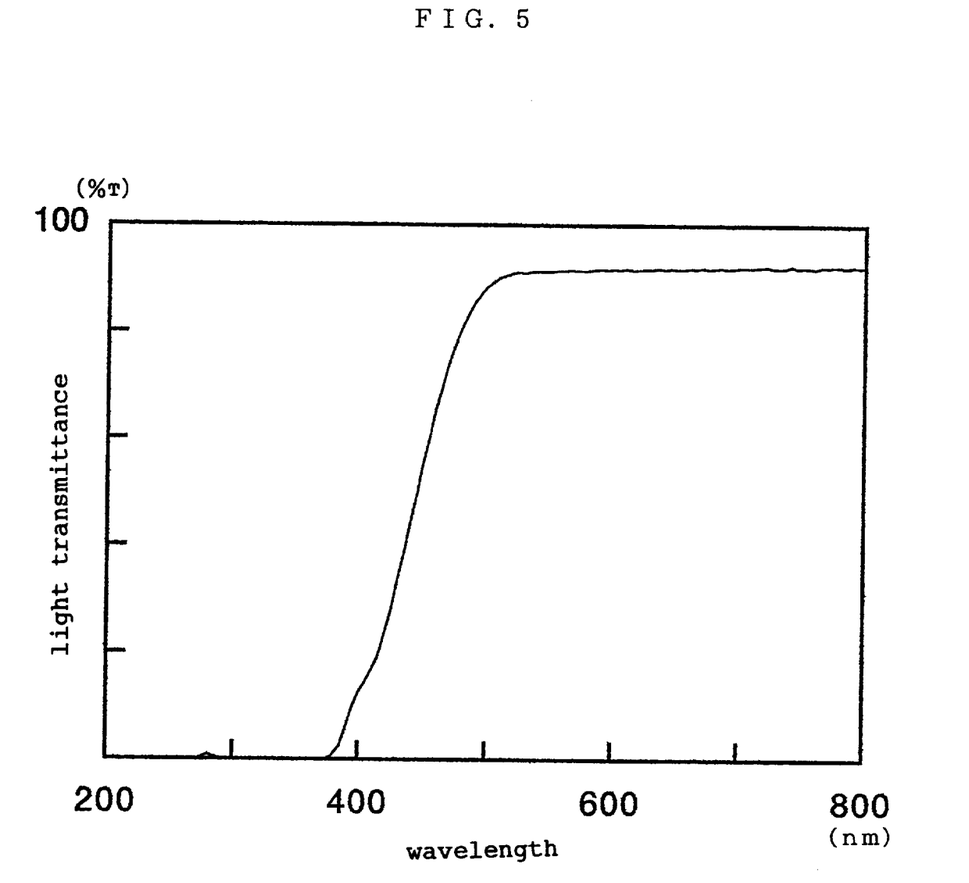
FIG. 5 shows a light transmittance curve of an ophthalmic plastic lens obtained in Example 9.

Then, a mixture containing 32 g of n-butyl acrylate (n-BA), 60 g of phenylethyl methacrylate (PEMA), 8 g of perfluorooctylethyloxypropylene methacrylate (HRM-5131HP), 3 g of ethylene glycol dimethacrylate (EDMA) and 0.3 g of AIBN was provided. To the mixture were added 0.15% by weight, based on the total amount of the monomers for a lens, of an ultraviolet absorbent CVPT and 0.02% by weight, based on the total amount of the monomers for a lens, of the reactive yellow dye HMPO-H, and the resultant mixture was fully stirred, to obtain a polymerizable material. The polymerizable material was added to the central portion of the above-prepared doughnut-shaped button, and thermally polymerized according to the polymerization program as described in Example 8. The resultant polymerizate had a central portion (diameter 3 mm) formed of a soft material colored in yellow and a circumferential portion formed of a hard material colored in blue. Then, the polymerizate was cut and polished in the form of an intraocular lens, to give a one-piece soft intraocular lens having an optic portion formed of a soft yellow material and a haptic portion formed of PMMA. The obtained lens was measured for a light transmittance to show a remarkably excellent light transmittance curve, as shown in FIG. 5.

The pyrazolone compound of the formula (I) provided by the present invention is a reactive yellow dye which has excellent copolymerizability and which exhibits excellent absorption spectrum in a region of 400 to 500 nm in a small amount. Therefore, the ophthalmic plastic lens of the present invention, obtained by polymerizing a polymerizable material containing the above pyrazolone compound and a monomer for a lens is colored in yellow and is free from the elusion of the yellow dye in an organic solvent, so that it is remarkably useful for an intraocular lens, particularly for a cyanopsia-correcting soft intraocular lens. To sum up, according to present invention, there can be provided an ophthalmic plastic lens remarkably excellent in view of function and safety.

What is claimed is:

1. A pyrazolone compound which is a compound of the formula (I), (I)

wherein X is phenyl or 4-alkylphenyl.

2. The pyrazolone compound of claim 1, wherein the 4-alkylphenyl is p-tolyl, 4-ethylphenyl, 4-n-propylphenyl, 4-isopropylphenyl, 4-n-butylphenyl, 4-isobutylphenyl, 4-sec-butylphenyl or 4-tert-butylphenyl.

3. The pyrazolone compound of claim 1, wherein the compound of the formula (I) is a diketo tautomer or one of two keto-enol tautomers represented by the formulas:

4. The pyrazolone compound of claim 1, wherein the compound of the formula (I) has solubility in, and copolymerizability with, a monomer for a lens.

5. The pyrazolone compound of claim 1, wherein the compound of the formula (I) is a reactive yellow dye having light absorption spectrum in a region of 400 to 500 nm.

6. The pyrazolone compound of claim 1, wherein the compound of the formula (I) is free from elution with a solvent when used for an ophthalmic plastic lens.

7. An ophthalmic plastic lens which is a polymerization product from a polymerizable material containing a pyrazolone compound of the formula (1) and a monomer for lens, (I)

wherein X is phenyl or 4-alkylphenyl.

8. The ophthalmic plastic lens of claim 7, which is an intraocular lens.

9. The ophthalmic plastic lens of claim 8, wherein the intraocular lens is a soft intraocular lens.

10. The ophthalmic plastic lens of claim 8, wherein the intraocular lens is a cyanopsia-correcting intraocular lens.

11. The ophthalmic plastic lens of claim 7, wherein the polymerizable material contains the pyrazolone compound of the formula (I) and the monomer for a lens in a pyrazolone compound/monomer amount ratio of 0.005/100 to 0.10/100.

12. The ophthalmic plastic lens of claim 7, wherein the polymerizable material contains an ultraviolet absorbent and a polymerization initiator.

13. The ophthalmic plastic lens of claim 12, wherein the ultraviolet absorbent has a monomer structure.

14. The ophthalmic plastic lens of claim 12, wherein the polymerizable material contains the ultraviolet absorbent in an amount of 0.05 to 5.0% by weight based on the monomer for a lens.

15. The ophthalmic plastic lens of claim 12, wherein the polymerization initiator is a radical-generating agent selected from a peroxide or a diazo compound or a photopolymerization initiator.

16. The ophthalmic plastic lens of claim 12, wherein the polymerizable material contains the polymerization initiator in an amount of 0.05 to 2.0% by weight based on the monomer for a lens.

17. The ophthalmic plastic lens of claim 7, wherein the ophthalmic plastic lens substantially does not cause elution of the pyrazolone compound of the formula (I), an ultraviolet absorbent and a polymerization initiator and has light absorption spectrum in a region of 400 to 500 nm.

18. The ophthalmic plastic lens of claim 7, wherein the lens or its optic portion is modified to have a hydrophilic surface by plasma-treating the lens or the optic portion with oxygen or air and immersing it in a reducing bath.

19. A process for the production of an ophthalmic plastic lens, which comprises casting a polymerizable material containing a pyrazolone compound of the formula (I) and a monomer for a lens into a mold in the form of a rod, a plate or a lens and polymerizing the polymerizable material, (I)

wherein X is phenyl or 4-alkylphenyl.

20. The process of claim 19, wherein the polymerizable material contains the pyrazolone compound and the monomer for a lens in a pyrazolone compound/monomer amount ratio of 0.005/100 to 0.10/100.

21. The process of claim 19, wherein the polymerizable material contains an ultraviolet absorbent and a polymerization initiator.

22. The process of claim 21, wherein the ultraviolet absorbent has a monomer structure.

23. The process of claim 21, wherein the ultraviolet absorbent is used in an amount of 0.05 to 5.0% by weight based on the monomer for a lens.

24. The process of claim 21, wherein the polymerization initiator is a radical-generating agent selected from a peroxide or a diazo compound or a photopolymerization initiator.

25. The process of claim 21, wherein the polymerization initiator is used in an amount of 0.05 to 2.0% by weight based on the monomer for a lens.

26. The process of claim 19, wherein the ophthalmic plastic lens does not cause elution of the pyrazolone compound of the formula (I), an ultraviolet absorbent and a polymerization initiator and has light absorption spectrum in a region of 400 to 500 nm.

27. The process of claim 19, wherein the mold is made of a metal, a plastic or a glass.

28. The process of claim 19, wherein the polymerization is carried out at a temperature in the range of 40 to 120° C.

29. The process of claim 19, wherein oxygen in the polymerizable material is replaced with an inert gas selected from nitrogen, argon or helium and the mold is closed before the polymerization is carried out.

30. A process for the production of an ophthalmic plastic lens, which comprises casting a polymerizable material containing the pyrazolone compound of the formula (I) and a monomer for a lens into a central hollow portion of a hard polymer material shaped in the form of a doughnut, polymerizing the polymerizable material and then cutting and polishing a polymerizate integrated with said hard polymer material, to form a hard haptic portion and a soft optic portion, (I)

wherein X is phenyl or 4-alkylphenyl.

31. The process of claim 30, wherein the hard polymer material is a colored product.

32. The process of claim 30, wherein the polymerizable material contains the pyrazolone compound and the monomer for a lens in a pyrazolone compound/monomer amount ratio of 0.005/100 to 0.10/100.

33. The process of claim 30, wherein the polymerizable material contains an ultraviolet absorbent and a polymerization initiator.

34. The process of claim 33, wherein the ultraviolet absorbent has a monomer structure.

35. The process of claim 33, wherein the ultraviolet absorbent is used in an amount of 0.05 to 5.0% by weight based on the monomer for a lens.

36. The process of claim 33, wherein the polymerization initiator is a radical-generating agent selected from a peroxide or a diazo compound or a photopolymerization initiator.

37. The process of claim 33, wherein the polymerization initiator is used in an amount of 0.05 to 2.0% by weight based on the monomer for a lens.

38. The process of claim 30, wherein the ophthalmic plastic lens does not cause elution of the pyrazolone compound of the formula (I), an ultraviolet absorbent and a polymerization initiator and has light absorption spectrum in a region of 400 to 500 nm.

39. The process of claim 30, wherein the polymerization is carried out at a temperature in the range of 40 to 120° C.

40. The process of claim 30, wherein oxygen in the polymerizable material is replaced with an inert gas selected from nitrogen, argon or helium and the mold is closed before the polymerization is carried out.

* * * * *